United States Patent [19]

Schnatterer et al.

[11] Patent Number: 4,929,766

[45] Date of Patent: May 29, 1990

[54] PROCESS ARE THE PREPARATION OF P-HYDROXY-BENZALDEHYDES

[75] Inventors: Albert Schnatterer; Helmut Fiege, both of Leverkusen, Fed. Rep. of Germany

[73] Assignee: Bayer Aktiengesellschaft, Leverkusen, Fed. Rep. of Germany

[21] Appl. No.: 311,481

[22] Filed: Feb. 16, 1989

[30] Foreign Application Priority Data

Feb. 24, 1988 [DE] Fed. Rep. of Germany ....... 3805697

[51] Int. Cl.$^5$ .............................................. C07C 45/36
[52] U.S. Cl. .................................... 568/432; 568/431
[58] Field of Search ........................ 568/432, 431, 433

[56] References Cited

U.S. PATENT DOCUMENTS

| | | | |
|---|---|---|---|
| 3,073,867 | 1/1963 | Offenhauer et al. | 568/432 |
| 3,666,815 | 5/1972 | Scheltus | 568/432 |
| 4,453,016 | 6/1984 | Au et al. | 568/432 |
| 4,471,140 | 9/1984 | Au | 568/432 |
| 4,481,374 | 11/1984 | Christidis et al. | 568/432 |
| 4,772,754 | 9/1988 | Röhrscheid | 568/432 |

FOREIGN PATENT DOCUMENTS 213544  6/1987  Japan ................................. 568/432

OTHER PUBLICATIONS

Patent Abstracts of Japan, Band 11, Nr. 365(C-460) [2812], 27. Nov. 1987; & JP-A-62 135 443 (C K Fine Kemikaruzu K.K.) 18-06-1987 *Zusammenfassung*.

*Primary Examiner*—Werren B. Lone
*Attorney, Agent, or Firm*—Sprung Horn Kramer & Woods

[57] ABSTRACT p-Hydroxy-benzaldehydes can be obtained by oxidation of the corresponding p-cresols with oxygen in the presence of basic substances in a solvent, the reaction being carried out in the additional presence of a chelate complex of iron and/or manganese. If desired, the reaction can be carried out in the presence of further metal salts.

20 Claims, No Drawings

PROCESS ARE THE PREPARATION OF P-HYDROXY-BENZALDEHYDES

BACKGROUND OF THE INVENTION

The invention relates to an improved process for the preparation of p-hydroxy-benzaldehyde and its derivatives by oxidation of the corresponding p-cresols with oxygen in the presence of chelate complexes of iron and/or manganese.

p-Hydroxy-benzaldehydes are important intermediates for industrial syntheses of flavours, plant-protection products, dyestuffs and pharmaceuticals.

It is possible to prepare p-hydroxy-benzaldehydes by oxidation of p-cresols, the selective oxidation with air oxygen being of industrial interest.

According to EP 0,012,936, p-cresol derivatives can be oxidized in a liquid phase in the presence of a base and a cobalt compound or metallic cobalt and an alcohol as the solvent with oxygen to p-hydroxy-benzaldehydes. For example, using 1 mol % of cobalt chloride and 3 mol of sodium hydroxide, relative to the p-cresol used, a selectivity of p-hydroxybenzaldehyde of 78% is obtained at a conversion of 92%.

According to U.S. Pat. No. 4,453,016, this process is improved by using a salt of the metals cobalt, manganese, nickel or chromium in combination with activated carbon. In the example listed there, 6.7 mol % of cobalt chloride and 6.7% by weight of activated carbon, relative to the p-cresol used, are employed. The addition of activated carbon increases the reaction rate. According to U.S. Pat. No. 4,471,140, the addition of an amine is also active in the same manner.

An improvement in the selectivity compared to the oxidation of p-cresol to p-hydroxy-benzaldehyde with oxygen, which is catalyzed by cobalt, is obtained, according to JP 61/24,535 (1986) by carrying out the oxidation in the presence of a combination from a cobalt and a copper compound. By using a total of 1.5% by weight of cobalt and copper salt, a selectivity of 87% of p-hydroxy-benzaldehyde at a p-cresol conversion of 97% is obtained. According to JP 62/153,240 (1987), the amount of the cobalt compound used can be reduced to one-tenth if the iron ion content is simultaneously maintained under 6 ppm.

According to JP 62/132,836 (1987), the oxidation of p-cresol to p-hydroxy-benzaldehyde is carried out in the presence of a mixture of an iron(III) and a nickel(II) compound, which achieves the establishment of equilibrium more rapidly. The selectivities are 52–81% and the conversions 42–54%. According to JP 62/135,443 (1987), the oxidation is carried out in the presence of iron(III) compounds, preferably iron(III) salts, thus achieving a selectivity of 40–60% at 40–50% of conversion.

The previous processes have the disadvantage that (a) in some cases significant amounts, in most cases about 1 mol %, relative to p-cresol, of the catalytically active heavy metal are used, water-soluble salts being preferably used, and (b) the p-hydroxy-benzaldehyde selectivities are in part only moderate.

In all these processes, during the subsequent aqueous work-up, the heavy metal salts end up in the waste water, which makes this waste water difficult to dispose of and loses the catalyst metals.

SUMMARY OF THE INVENTION

A process for the preparation of p-hydroxy-benzaldehydes of the formula

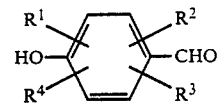

has been found,
in which
$R^1$ to $R^4$ independently of one another denote hydrogen, halogen, $C_1-C_{10}$-alkyl, $C_3-C_8$-cycloalkyl, phenyl or $C_1-C_{10}$-alkoxy, by oxidizing p-cresols of the formula

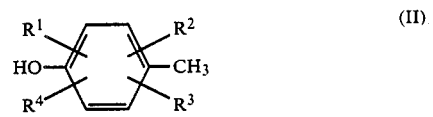

(II)

in which
$R^1$ to $R^4$ have the meaning given, with oxygen in the presence of basic substances in a solvent, which is characterized in that the oxidation is carried out in the presence of a chelate complex of iron, manganese or iron and manganese.

DETAILED DESCRIPTION OF THE INVENTION

The process according to the invention has the following advantages:

1. p-hydroxy-benzaldehydes can be prepared from their corresponding p-cresols with high selectivity;
2. the amounts of metal necessary to carry out the process are significantly less than in previous processes; and
3. the catalyst can be recycled and thus represents a significant progress in terms of ecology.

p-Cresols which can be used according to the invention are those of the formula (I).

Halogen can be fluorine, chlorine, bromine or iodine, preferably fluorine, chlorine or bromine.

Examples of alkyl groups in $C_1-C_{10}$-alkyl or $C_1-C_{10}$-alkoxy are methyl, ethyl, propyl, isopropyl, n-butyl, i-butyl, t-butyl, hexyl, octyl or decyl. Preferably, these alkyl groups have 1–6 C atoms, particularly preferably 1–4 C atoms.

$C_3-C_8$-Cycloalkyl comprises cyclopropyl, cyclopentyl, cyclohexyl, cyclooctyl and derivatives thereof which are mono- or disubstituted by methyl or ethyl; preference is given to $C_5-C_6$-cycloalkyl which can be substituted by methyl.

Phenyl can be mono- or disubstituted by halogen of the type mentioned, by $C_1-C_4$-alkyl of the type mentioned or by nitro.

Preferably, the p-cresols used are those of the formula

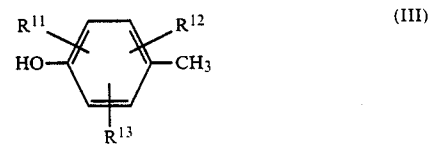

(III)

in which $R^{11}$, $R^{12}$ and $R^{13}$ independently of one another denote hydrogen, fluorine, chlorine, bromine, $C_1$–$C_6$-alkyl, $C_5$–$C_6$-cycloalkyl, phenyl or $C_1$–$C_6$-alkoxy.

Particularly preferably, the p-cresols used are those of the formula

(IV)

in which $R^{21}$ stands for hydrogen, fluorine, chlorine, bromine, $C_1$–$C_6$-alkyl, cyclohexyl, phenyl or $C_1$–$C_6$-alkoxy, $R^{22}$ denotes hydrogen, $C_1$–$C_6$-alkyl or $C_1$–$C_6$-alkoxy.

Important p-cresols which are, however, only mentioned by way of examples are: 2-bromo-p-cresol, 3-chloro-p-cresol, 2,4-dimethylphenol, 3,4-dimethylphenol, 2,4,5-trimethylphenol, 2,4,6-trimethylphenol, 2,6-dimethoxy-p-cresol, 2-tert.-butyl-p-cresol, 2,6-di-tert.-butyl-p-cresol, 2-chloro-6-isopropyl-p-cresol. Very particularly preferably, p-cresol is used.

The process according to the invention makes it possible to selectively oxidize only the methyl group which is in the p-position relative to the OH group to give the formyl group. The other substituents, including methyl groups, remain unchanged. Because of this selectivity, mixtures of cresols also containing o- or m-cresols in addition to the substituted or unsubstituted p-cresol are also suitable as starting materials. The isomers which do not react according to the invention, with the exception of the p-cresol, remain essentially unchanged.

The catalyst used in the process according to the invention is a chelate complex of iron and/or manganese in which the iron or the manganese can be present in the divalent, trivalent or tetravalent state. The chelate ligands can be bidentate to hexadentate. The metal in the chelate complex can be 4-, 5- or 6-coordinate. The coordinating positions in the ligand can be the elements N, O, S, P, Se, As, preferably N and O.

Examples of these chelating ligands are: ethylenediamine, diethylenetriamine, triethylenetetramine, 2,2-dipyridyl, 1,10-phenanthroline, terpyridyl, carboxylates, oxalate, 1,2-bis-(diphenylphosphino)-ethane, β-diketonates, for example acetyl acetonate and Schiff bases derived therefrom, dioximes of α-diketones, for example dimethylglyoxime, tropolonate complexes and Schiff bases derived therefrom; triketones, for example 2,4,6-heptanetrione and Schiff bases derived therefrom; Schiff bases derived from salicylic aldehyde, for example ethylenebis(salicylic aldimine); Schiff bases derived from acetoacetylphenol and 2,6-diformylpyridine; chelate complexes with the ligands N,N,N',N'-tetrakis[(2-benzimidazolyl)methyl]alkanediamine, polyphosphates, pyridine-2-carboxylate, ethylenediaminetetraacetate. Preferably, macrocyclic polyethers and polysulphides, porphyrin analogues, macrocycles obtainable by condensation of carbonyl compounds with amines, for example tetrabenzo[b,f,j,n]-[1.5.9.13]-tetraazacyclohexadecyne as the self-condensation product of o-aminobenzaldehyde are used. Particular preference is given to prophyrins and related chemically modified systems, for example corrins, phlorins, oxophlorins, porphyrinogens, azoporphyrins, benzoporphyrins, chlorins.

The porphyrins can be of natural origin, for example haematoporphyrin, deuteroporphyrin, protoporphyrin, uroporphyrin, coproporphyrin or of purely synthetic nature, for example octaethylporphyrin. Synthetic porphyrins are preferably used, particularly preferably meso-tetraarylporphyrins, for example tetraphenylporphin (TPP), tetrakis-(4-methoxyphenyl)-porphin, tetrakis-(2,4-dimethoxyphenyl)-porphin, tetrakis-(3,4-methylenedioxyphenyl)-porphin, tetrakis-(4-methylphenyl)-porphin, tetrakis-(2-chlorophenyl)-porphin, tetrakis-(pentafluorophenyl)-porphin are used.

It is not absolutely necessary that each coordination position in the metal chelate complex be occupied by a chelating ligand. Free coordination positions can be occupied by any desired donor, for example by anions of inorganic and organic acids such as $OH^-$, $Cl^-$, $Br^-$, $F^-$, $I^-$, $N_3^-$, $NO_3^-$, $NO_2^-$, $SO_4^{2-}$, $SO_3^-$, phosphate, borate, carboxylate, by amines such as triethylamine, pyridine, piperidine, imidazole, by sulphides such as dimethyl sulphide, dimethyl sulphoxide.

The chelate complexes can have one or more metal centres and they can be dimers, oligomers or polymers. Dimerization, oligomerization or polymerization can occur by bridge formation between the metal centres via donor molecules or by crosslinking of the chelating ligands with one another. The metal centres can be, for example, oxo- or peroxo-bridged. Examples of oxo-bridged iron and manganese chelate complex dimers are $(FeTPP)_2O$, $(MnTPP)_2O$, $(FePc)_2O$, $(MnPc)_2O$ (TPP=tetraphenylporphyrin, Pc=phthalocyanine). The chelate complexes can be crosslinked through a polymer carrier, for example through an appropriately functionalized polystyrene.

The metal chelate complex can also be used in combination with a surface-active substance, for example activated carbon.

The molar ratio of iron and/or manganese chelate complex to p-cresol used is 0.000001–0.05, preferably 0.00001–0.005, calculated as metal. Surprisingly, the iron and/or manganese chelate complex is highly active even in extremely small amounts. The working examples listed below clearly show that the use of simple iron or manganese salts and also the use of simple iron or manganese complexes or complex salts has only a comparatively small effect in the oxidation of p-cresols to p-hydroxybenzaldehydes with oxygen in the process according to the invention. Simple iron or manganese salts are understood to mean: salts of inorganic and organic acids, in the form of hydrates as well as in anhydrous form, for example $FeCl_3 \times 6H_2O$, $FeCl_2 \times 4H_2O$, $FeSO_4 \times 7H_2O$, $Fe_2(SO_4)_3 \times H_2O$, $Fe(NO_3)_3 \times 9H_2O$, iron phosphates $Mn(OAc)_2 \times 4H_2O$, $Mn(OAc)_3 \times 2H_2O$, $MnCl_2 \times 4H_2O$, $MnSO_4 \times 4H_2O$, $MnCO_3$, $Mn(NO_3)_2 \times 6H_2O$. Examples of simple iron or manganese complexes or complex salts which also have only a small effect are: $K_3Fe(CN)_6$, $NaFeCN_5NO$, $K_2MnF_6$.

It is thus even more surprising that chelate complexes of iron and/or manganese display, in the process according to the invention, such a completely unexpected high efficiency and even in extremely small concentrations; this is in particular true for the iron and manganese porphyrins. At high reaction rates and high degrees of conversion, high p-hydroxybenzaldehyde selectivities are achieved; this is in particular true if preferably the iron and/or manganese chelate complex, in particular the corresponding porphyrin complex, is used in combination with one of the co-catalysts mentioned below.

These co-catalysts, which can be advantageously but not absolutely necessarily used in the process according to the invention, are compounds of the metals copper, chromium, nickel, silver, vanadium, niobium, tantalum, cadmium, cerium or other lanthanides such as neodymium or praseodymium. It is furthermore very surprising that even the use of iron and/or manganese compounds, although these metals are already present according to the invention in the chelate complexes, in addition to these chelate complexes effect a further improvement of the process according to the invention. These metal compounds can be added individually or several of these can be added in any desired combinations as co-catalysts. The metal in these compounds can adopt any of the oxidation states individually possible. These metal compounds can be used in the form of the metal salts of inorganic acids, for example the halides such as fluorides, chlorides, bromides or iodides, the sulphates, nitrates, carbonates, phosphates, borates, sulphites, cyanides or of the salts of organic acids such as the acetates, stearates, oxalates, citrates or of ion exchangers containing these metals in bound form. Furthermore it is also possible to use metal complexes or complex salts and metal chelate metal complexes. It is furthermore very surprising that even the elemental metals are effective as co-catalysts in the same manner as the metal compounds.

Preferably, the co-catalysts used are the metal chelate complexes and the salts of inorganic or organic acids. What has been said with respect to the iron and/or manganese chelate complexes - the use of which is obligatory - applies to the use as metal chelate complexes. Of the metal salts, in particular the chlorides, sulphates, nitrates, acetates, oxides and hydroxides in the form of hydrates or in anhydrous form are preferably used. Furthermore, the metal salt can also be used in combination with a complexing agent, preferably in combination with ammonia or amines, for example copper chlorides together with tetramethylethylenediamine.

Particularly preferably, inorganic salts of copper and/or cerium are used as co-catalysts.

The amount used of the co-catalyst is not subject to any specific restriction. The noteworthy feature is the high activity even in very small concentrations. For example, a suitable molar ratio of co-catalyst to p-cresol used is 0.00001-0.1, preferably of 0.0001-0.01. The molar ratio of iron and/or manganese chelate complex to co-catalyst is non-specific and is chosen to be, for example, in the range 0.001-1000:1, preferably 0.01-100:1. If, on the other hand, the metal compounds mentioned as active as co-catalysts are used individually or in any desired combinations without the iron and/or manganese chelate complexes described, their activity in the oxidation of p-cresols is comparatively very small.

Suitable bases for the process according to the invention are all those which have a higher basicity than the p-cresolates which can be prepared from them, for example metal hydroxides, metal alcoholates and metal amides of alkali metals and alkaline earth metals and in the case of alcoholates and amides, of aluminium. Of the metals mentioned, important examples are sodium, potassium, lithium, calcium and magnesium. Suitable alcoholates are methylate, ethylate, isopropylate, tert.-butylate. Examples of amides are diethylamide, ethylamide, diisopropylamide, dibutylamide etc. Of the bases mentioned, the hydroxides and the alcoholates are preferred, in particular sodium hydroxide, potassium hydroxide, sodium methylate, sodium ethylate and potassium tert.-butylate are preferred.

The amount of base used is 1–10 equivalents of base per mole of p-cresol; preferably, 1.5–6 equivalents of base are used.

In practice, the use of a mixture of bases consisting of one of the alkali metal hydroxides or alkaline earth metal hydroxides mentioned and one of the alkali metal alcoholates mentioned turns out to be particularly advantageous. Preferred mixtures of bases are those consisting of an alkali metal hydroxide and an alkali metal alcoholate of methanol or ethanol. In particular, mixtures of sodium hydroxide or potassium hydroxide and sodium methylate are preferred. The composition of these mixture of bases in terms of alkali metal or alkaline earth metal hydroxide and alkali metal alcoholate contents, which represent an advantage compared to the use of, on the one hand, exclusively alkali metal hydroxide or alkaline earth metal hydroxide and, on the other, exclusively alkali metal alcoholate, can vary in the wide range of 1:50–50:1. Preferably, an equivalent ratio of alkali metal hydroxide to alkali metal alcoholate of 8:1–1:4, particularly preferably 4:1–2:3, is used.

Solvents for the process according to the invention are those which under the reaction conditions do not react or react only very slowly with oxygen and dissolve the starting components, for example alcohols, ethers, halogenated hydrocarbons, amines, amides, sulphoxides. These solvents can be used individually or in mixtures of two or several solvents. If these solvents are completely or partially water-miscible, such mixtures with water can also be used. Preferably, the alcoholic solvents are, for example, methanol, ethanol, isopropanol, butanol, tert.-butanol and/or ethylene glycol.

In the case where alcohols are used as solvents, substituted or unsubstituted p-hydroxy-benzyl alkyl ethers of the formula

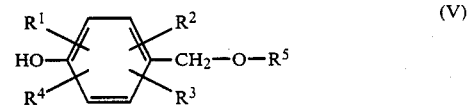

(V)

in which
$R^1$ to $R^4$ have the abovementioned range of definitions and
$R^5$ is the alkyl radical of the alcohols used as the solvent are found in the reaction mixture.

The amount of these ethers varies with the reaction conditions.

The oxygen used for the process according to the invention can be pure oxygen or oxygen in diluted form, for example in the form of oxygen-containing gases. The economically most favourable form of the oxygen usable according to the invention is air. The pressure of the oxygen or of the oxygen-containing gas is not subject to any special restriction and can be 1–100 bar, preferably 1–10 bar. If oxygen-containing gases are used, the oxygen content is also not subject to any restriction. Primarily, it is dependent on operational factors such as operational safety and reaction rate. The oxygen can be, for example, fed into the reaction medium, for example by using sintered glass crucibles; however, it is also possible to absorb it into the reaction mixture by vigorous stirring.

The reaction temperature can vary widely, for example from 0°–200° C., preferably 20°–100° C.

In the work-up which follows the process according to the invention, the catalysts are first separated off from the reaction mixture (for example by filtration or centrifugation) and, if desired, used again; furthermore, unconverted p-cresol and the portion of the reaction mixture which had only been oxidized to the stage of the p-hydroxybenzyl alkyl ether is returned to a subsequent batch.

The type of work-up depends on the conditions under which the reaction has been carried out. If the metal chelate complex is, for example, sparingly soluble in the solvent used, such as iron tetraphenylporphin in methanol, it can, together with the co-catalyst, which, depending upon in which form it had been used, for example as a metal salt, is afterwards present as insoluble oxide hydrate, be filtered off directly from the reaction mixture, which, if necessary, had been sufficiently diluted to dissolve starting material and product. The filtrate can subsequently be evaporated, taken up in water, and the p-hydroxybenzaldehyde liberated by acidification.

If the metal chelate complex is readily soluble in the solvent used, such as, for example, manganese tetraphenylporphin in methanol, but is water-insoluble, the solvent can be evaporated from the reaction mixture, the residue taken up in water, and the metal chelate complex together with the co-catalyst present as insoluble oxide hydrate filtered off. Since products and starting materials are present in the form of their salts (phenolates), they are sufficiently water-soluble. From the filtrate, the p-hydroxybenzaldehyde can again be liberated by acidification.

In an even further variation, water can be added directly to the reaction mixture (provided sufficient miscibility with the solvent can be achieved) and the water-insoluble metal chelate complex together with the co-catalyst present as oxide hydrate can be filtered off. The organic solvent is removed from the filtrate, for example by distillation, and from the aqueous-alkaline solution, the p-hydroxybenzaldehyde is liberated by acidification.

Particularly advantageous embodiments are: methanol as solvent, sodium hydroxide, sodium methylate, potassium hydroxide or mixtures thereof as base, iron tetraphenylporphin as metal chelate complex and a copper compound such as $CuCl_2 \times 2H_2O$ or CuO as co-catalyst.

A preferred work-up variation consists in drying the reaction mixture by spraying, dissolving the soluble components of the dry residue in hot water and then filtering off the iron tetraphenylporphin and the insoluble copper oxide hydrate and, if desired, recycling them. In general, 2–50, preferably 3–20, parts by weight of water per 1 part by weight of p-cresol used for the oxidation are added to the reaction mixture. In the case where the sodium salt or potassium salt of p-hydroxybenzaldehyde is sparingly soluble in cold water, the solution is heated to 50°–90° C. and filtered at this temperature. In a variation of this type of work-up, the water can be added directly to the reaction mixture, the resulting solution heated to 50°–90° C., and the iron tetraphenylporphin together with the oxide hydrate of copper filtered off.

In an even further work-up variation, the reaction mixture is diluted with methanol to the 1.5–5-fold volume, the solution is heated, preferably to 40°–65° C., and the sparingly soluble iron tetraphenylporphin together with the insoluble oxide hydrate of copper is filtered off. The filtrate is then dried by spraying, and the residue is taken up in water.

All work-up variations listed here can be modified in such a manner that before the iron and/or manganese chelate complex and the co-catalysts present as metal oxide hydrates are filtered off the pH of the strongly alkaline solution is adjusted to a value between 9–13 by acidification. By means of this measure, the solubility of the metal compounds can be reduced if necessary.

From the aqueous-alkaline solution, p-hydroxybenzaldehyde and any present p-hydroxybenzyl alkyl ether and unconverted p-cresol are liberated by acidification. The removal and purification of p-hydroxybenzaldehyde can be carried out by known methods, for example by fractional crystallization, if necessary with the aid of the method of bisulphite adduct formation.

Very pure p-hydroxybenzaldehyde can be produced by extraction of the crude product with aqueous bisulphite solution, followed by liberation of p-hydroxybenzaldehyde by acidification.

The removal and purification of p-hydroxybenzaldehyde in combination with the process according to the invention can be achieved in a particularly simple manner by passing $SO_2$ directly into the alkaline solution being present in the process according to the invention after the catalysts have been filtered off, for example until the solution has reached a pH of 2. By means of extraction with a suitable organic solvent, unconverted p-cresol or, in the case where cresol mixtures had been used, the unconverted o- and m-isomers and also the p-hydroxybenzyl methyl ether and resinous products can then be separated off. The $SO_2$ is then driven out of the aqueous solution by acidification and heating, and p-hydroxybenzaldehyde is liberated.

EXAMPLE 1

A mixture of 10.8 g (0.1 mol) of p-cresol, 12.0 g (0.30 mol) of sodium hydroxide, 25 g of methanol and 0.10 g (0.14 mmol) of iron tetraphenylporphin (in the form of FeTPPCl) was stirred in an oxygen atmosphere at atmospheric pressure and 60° C. for 2.5 hours.

The methanol was subsequently distilled off under reduced pressure, the residue taken up in 70 ml of water, the solution heated to 70° C. and filtered. From the filter, 0.092 g of iron tetraphenylporphin could be recovered after drying. The filtrate was acidified with dilute sulphuric acid, and the product was extracted with ethyl acetate. After evaporation of the ethyl acetate in vacuo from the organic phase, 11.04 g of product containing (determined by HPLC=high-pressure liquid chromatography) 9.0% of cresol, 55.5% of p-hydroxybenzaldehyde, 5.3% of p-hydroxybenzyl methyl ether remained. This corresponds to a cresol conversion of 90.8%, a p-hydroxybenzaldehyde selectivity of 55.3% and a p-hydroxybenzyl methyl ether selectivity of 4.7%.

EXAMPLE 2

Procedure as in Example 1, except that 1.0 g of activated carbon was added. The reaction was stopped after 4 hours, and the reaction mixture worked up as in Example 1. This gave 10.36 g of a crude product containing 80.1% of p-hydroxybenzaldehyde, 7.2% of p-hydroxybenzyl methyl ether, 2.0% of p-cresol. Hence, the p-hydroxybenzaldehyde selectivity was 69.3%, the p-hydroxybenzyl methyl ether selectivity 5.5% at a p-cresol conversion of 98.1%.

EXAMPLE 3

A mixture of 10.8 g (0.10 mol) of p-cresol, 12.0 g (0.30 mol) of sodium hydroxide, 25 g of methanol, 0.10 g (0.14 mmol) of iron tetraphenylporphin (in the form of FeTPPCl) and 0.043 g (0.25 mmol) of $CuCl_2 \times 2H_2O$ were stirred in an oxygen atmosphere at atmospheric pressure and 60° C. for 7 hours.

The reaction mixture was worked up as in Example 1 and had the following result:
  p-cresol conversion: 96.4%
  p-hydroxybenzaldehyde selectivity: 78.2%
  p-hydroxybenzyl methyl ether selectivity: 3.4%

EXAMPLE 4

A mixture of 10.8 g (0.10 mol) of p-cresol, 12.0 g (0.30 mol) of sodium hydroxide, 25 g of methanol, 0.10 g (0.14 mmol) of iron tetraphenylporphin (in the form of FeTPPCl), 0.043 g (0.25 mmol) of $CuCl_2 \times 2H_2O$ and 0.137 g (0.25 mmol) of $(NH_4)_2 Ce(NO_3)_6$ were stirred in an oxygen atmosphere at atmospheric pressure and 60° C. for 7 hours.

The reaction mixture was worked up as in Example 1.
Result:
  p-cresol conversion: 98.8%
  p-hydroxybenzaldehyde selectivity: 82.0%
  p-hydroxybenzyl methyl ether selectivity: 0.3%

EXAMPLE 5

Materials and procedure as in Example 3. The removal and purification of p-hydroxybenzaldehyde was carried out via the bisulphite adduct in the manner described below: after the introduction of the oxygen was finished, the methanol was distilled off from the reaction mixture, the residue taken up in 70 ml of water, the solution heated to 70° C. and filtered. After washing the filter residue with water and drying, 0.115 g of catalyst mixture remained on the filter consisting of iron tetraphenylporphin and copper oxide hydrate. At room temperature, $SO_2$ was then passed into the alkaline filtrate until a pH of 2 had been reached. Stirring was then continued for 1 hour, and the mixture was then extracted twice with ethyl acetate. The resulting organic phase was dried over sodium sulphate, and the solvent distilled off. 2.31 g of an oil remained as the residue having the composition (yield):
  p-cresol: 2.8% (0.6%)
  p-hydroxybenzaldehyde: 11.7% (2.2%)
  p-hydroxybenzyl methyl ether: 32.1% (5.4%)

The aqueous phase was acidified with 50 ml of concentrated HCl, and the $SO_2$ was removed as completely as possible by heating and by applying a slight vacuum. The liberated p-hydroxybenzaldehyde was extracted from the aqueous phase by extracting it three times with ethyl acetate, the organic phase deacidified by washing with bicarbonate solution, dried over sodium sulphate and evaporated. 8.74 g of a colourless fine-crystalline product containing 99.4% of p-hydroxybenzaldehyde (yield 71.2%) remained as a residue.

EXAMPLES 6–16

A mixture of 10.8 g (0.10 mol) of p-cresol, 12.0 g (0.30 mol) of sodium hydroxide, 25 g of methanol, 0.10 g (0.14 mmol) of iron tetraphenylporphin (in the form of FeTPPCl) and 0.25 mmol of the metal compounds listed in Table 1 were vigorously stirred in an oxygen atmosphere at atmospheric pressure and 60° C. for the number of hours also listed in Table 1. The reaction mixture was worked up as in Example 1 and analyzed by means of HPLC. Table 1 shows the results with respect to the p-cresol conversion and the selectivities in the formation of p-hydroxybenzaldehyde (p-HBA) and p-hydroxybenzyl methyl ether (p-HBME).

TABLE 1

| Example No. | Metal compound | Reaction time (h) | Conversion % | Selectivity % p-HBA | Selectivity % p-HBME |
|---|---|---|---|---|---|
| 6 | $(NH_4).Ce(NO_3)_6$ | 6 | 96.2 | 74.6 | 2.8 |
| 7 | $Mn(OAc)_2.4H_2O$* | 7 | 91.1 | 62.9 | 11.7 |
| 8 | $Cr(NO_3)_3.9H_2O$ | 7 | 88.1 | 57.5 | 12.2 |
| 9 | $FeCl_2.4H_2O$ | 7 | 91.6 | 61.8 | 15.5 |
| 10 | $Ni(NO_3)_2.6H_2O$ | 7 | 96.0 | 58.4 | 17.2 |
| 11 | VO(acac)* | 7 | 96.9 | 68.7 | 11.9 |
| 12 | AgOAc* | 7 | 94.8 | 53.3 | 17.8 |
| 13 | $NbCl_5$ | 7 | 98.6 | 63.9 | 3.1 |
| 14 | $TaCl_5$ | 7 | 99.4 | 70.2 | 11.6 |
| 15 | $Cd(NO_3)_2.4H_2O$ | 7 | 95.1 | 61.2 | 12.1 |
| 16 | $Nd(NO_3)_2.6H_2O$ + $Pr(NO_3)_3.6H_2O$ (7:3) | 7 | 94.9 | 62.1 | 18.6 |

*Ac = acetyl, acac = radical of acetyl acetonate

EXAMPLES 17–25 (COMPARATIVE EXAMPLES)

In Examples 17 to 25, the activity of simple iron and manganese salts and the activity of some metal compounds used as co-catalysts without the addition of iron tetraphenylporphin but under otherwise identical conditions as in the previous examples were tested as comparison in the oxidation of p-cresol with oxygen.

A mixture of 10.8 g (0.10 mol) of p-cresol, 12.0 g (0.30 mol) of sodium hydroxide, 25 g of methanol and the metal salt mentioned in Table 2 in the amount given there was vigorously stirred in an oxygen atmosphere at atmospheric pressure and 60° C. for 7 hours. The results with respect to the p-cresol conversion and the selectivities in the formation of p-hydroxybenzaldehyde (p-HBA) and p-hydroxybenzyl methyl ether (p-HBME) are summarized in Table 2.

TABLE 2

| Example No. | Metal compound (amount added) | Conversion % | Selectivity % p-HBA | Selectivity % p-HBME |
|---|---|---|---|---|
| 17 | $FeSO_4.7 H_2O$ (2,5 mmol) | 25.7 | 41.8 | 7.0 |
| 18 | $K_3Fe(CN)_6$ (2,5 mmol) | 31.5 | 2.2 | 0.7 |
| 19 | $FeCl_3.6 H_2O$ (1 mmol) | 33.9 | 51.2 | 1.5 |
| 20 | $FeCl_3.6 H_2O$ (5 mmol) | 32.0 | 48.0 | 6.4 |
| 21 | $Ni(NO_3)_2.6 H_2O$ (1,0 mmol) | 10.9 | 7.2 | 2.5 |
| 22 | $Mn(OAc)_2.4 H_2O$ (1,0 mmol) | 16.2 | 9.2 | — |
| 23 | $Cr(NO_3)_3.9 H_2O$ (1,0 mmol) | 8.3 | 10.1 | — |
| 24 | $FeCl_3.6 H_2O$ (1,0 mmol) + $Ni(NO_3)_2.6 H_2O$ (1,0 mmol) | 33.3 | 48.9 | 0.4 |
| 25 | $CuCl_2.2 H_2O$ (1,0 mmol) | 33.9 | 12.1 | 4.7 |

EXAMPLE 26

Catalyst recycling: A mixture of 10.8 g (0.10 mol) of p-cresol, 12.0 g (0.30 mol) of sodium hydroxide, 25 g of methanol, 0.30 g (0.43 mmol) of iron tetraphenylporphin (in the form of FeTPPCl) and 0.128 g (0.75 mmol) of $CuCl_2 \times 2H_2O$ was stirred in an oxygen atmosphere at atmospheric pressure and 60° C. for 6 hours. The methanol was then distilled off under reduced pressure, the residue taken up in 70 ml of water, the solution heated to 70° C. and filtered. The filter residue was washed twice with 15 ml each of hot water, dried and added to the starting mixture in the next oxidation, which was carried out in the same manner, except that neither further iron tetraphenylporphin nor further copper chloride was used (not even as a replenishment with the exception of the 6th recycling). The work-up was carried out as in Example 1. In Table 3, the results of the catalyst re-cyclings are summarized. In the 6th recycling, another 0.04 g of $CuCl_2 \times 2H_2O$ was added as a replenishment. After the 10th recycling, the amount of catalyst still amounted to 0.14 g. 0.11 g of pure tetraphenylporphin could be isolated therefrom.

TABLE 3

|  | Conversion % | Selectivity % | |
|---|---|---|---|
|  |  | p-HBA | p-HBME |
| Example 26 | 91.2 | 56.7 | 2.4 |
| Recycling 1 | 96.2 | 64.2 | 15.76 |
| 2 | 94.5 | 63.6 | 9.7 |
| 3 | 91.7 | 67.0 | 10.7 |
| 4 | 95.4 | 64.5 | 16.7 |
| 5 | 95.7 | 59.3 | 7.4 |
| 6 | 88.8 | 62.4 | 10.4 |
| 7 | 95.9 | 60.5 | 9.0 |
| 8 | 92.0 | 66.4 | 13.9 |
| 9 | 90.5 | 61.9 | 3.2 |
| 10 | 89.6 | 73.9 | 0.2 |

EXAMPLES 27–31

A mixture of 10.8 g (0.10 mol) of p-cresol, 12.0 g (0.30 mol) of sodium hydroxide, 25 g of methanol and the metal complex mentioned in Table 5 in the amount stated there was stirred in an oxygen atmosphere at atmospheric pressure at 60° C. for 5–7 hours. The reaction mixture was worked up as in Example 1. As for the results, see Table 4.

TABLE 4

| Example No. | Metal compound (amount added in mmol) | Reaction time (h) | Conversion | Selectivity % | |
|---|---|---|---|---|---|
|  |  |  |  | p-HBA | p-HBME |
| 27 | MnTPPOL* (0.15 mmol) | 5 | 48.8 | 62.8 | 6.4 |
| 28 | (FeTPP)$_2$O** (0.15 mol) | 6 | 92.5 | 61.2 | 5.3 |
| 29 | Iron phthalocyanine (0.50 mmol) | 6 | 35.4 | 42.5 | 6.9 |
| 30 | Iron porphyrazine (0.30 mmol) | 7 | 33.7 | 64.6 | 15.5 |
| 31 | Haemin (0.30 mmol) | 7 | 56.1 | 48.5 | 3.9 |

*Manganese tetraphenylporphin charge balanced by Cl$^-$
**Oxygen-bridged iron porphyrin dimer; iron tetraphenylporphin whose charge was balanced by Cl$^-$ was treated with NaOH, thus forming the dimer having an oxygen bridge.

EXAMPLE 32

50 g of methanol, 24.0 g (0.60 mol) of sodium hydroxide, 0.20 g (0.28 mmol) of iron tetraphenylporphin (in the form of FeTPPCl) and 0.085 g (0.50 mmol) of $CuCl_2 \times 2H_2O$ were added to an m/p-cresol mixture consisting of 10.8 g (0.10 mol) of p-cresol and 10.8 g (0.10 mol) of m-cresol, and the entire mixture was vigorously stirred in an oxygen atmosphere at 60° C. and atmospheric pressure for 7 hours. The reaction mixture was worked up as in Example 1. Analysis showed the following result:

| p-cresol conversion: | 98.0% |
|---|---|
| p-hydroxybenzaldehyde selectivity: | 75.1% |
| p-hydroxybenzyl methyl ether selectivity: | 13.8% |
| m-cresol recovery: | 87.6% |

The reaction mixture contained neither 3-hydroxybenzaldehyde nor 3-hydroxybenzyl methyl ether.

EXAMPLES 33–36

0.10 mol each of the p-cresol derivatives listed in Table 5 together with 12.0 g (0.30 mol) of sodium hydroxide, 50 g of methanol, 0.10 g (0.14 mmol) of iron tetraphenylporphin (in the form of FeTPPCl) and 0.043 g (0.25 mmol) of $CuCl_2 \times 2H_2O$ were vigorously stirred in an oxygen atmosphere at 60° C. and atmospheric pressure for the number of hours given in Table 5. The reaction mixtures were worked up analogously to Example 1, and the products were analyzed. The degree of conversion of the corresponding p-cresols and the selectivities with respect to the formation of 4-hydroxybenzaldehyde derivatives are summarized in Table 5.

TABLE 5

| Example No. | p-Cresol derivative | Reaction time (h) | 4-Hydroxybenzaldehyde derivative | Selectivity (%) | Conversion (% 0) |
|---|---|---|---|---|---|
| 33 | 3-chloro-p-cresol | 5 | 2-chloro-4-hydroxybenzaldehyde | 72.7 | 95 |
| 34 | 2-bromo-p-cresol | 3 | 3-bromo-4-hydroxybenzaldehyde | 83.1 | 86 |
| 35 | 2-chloro-6-isopropyl-p-cresol | 5 | 3-chloro-5-isopropyl-4-hydroxybenzaldehyde | 67.2 | 98 |
| 36 | 2,6-di-t-butyl-p-cresol | 4 | 3,5-di-tert.-butyl-4-hydroxybenzaldehyde | 52.1 | 97 |

Examples 37–47 listed below were carried out in a larger reactor using proportionately higher methanol and base quantities, compared to Examples 1–36.

EXAMPLE 37

In a 1 l reactor, an oxygen stream of 5.0 l/h was passed into a mixture of 54.0 g (0.50 mol) of p-cresol, 250 g of methanol, 100 g (2.5 mol) of sodium hydroxide, 0.25 g (0.35 mmol) of iron tetraphenylporphin (in the form of FeTPPCl) and 0.10 g (1.3 mmol) of copper (II) oxide, which had been heated to 60° C., for 7 hours with vigorous stirring. During the entire duration of the reaction, the temperature was maintained at 60° C.

After the reaction was completed, the methanol was distilled off under reduced pressure, the residue taken up in 700 ml of water, adjusted to a pH of 11.5 with concentrated hydrochloric acid, then heated to 70° C. and filtered. After cooling to room temperature, the filtrate was acidified with concentrated hydrochloric acid and subsequently extracted with ethyl acetate. After evaporation of the ethyl acetate in vacuo, 60.8 g of crude product containing 76.9% of p-hydroxybenzaldehyde, 1.9% of p-hydroxybenzyl methyl ether and 0.4% of p-cresol remained.

Yield of p-hydroxybenzaldehyde: 76.6%.

EXAMPLE 38

Procedure as in Example 37, except that instead of sodium hydroxide 138 g (2.5 mol) of sodium methylate (98% pure) were used.

Conversion >99%.

Yield: 70.4% of p-hydroxybenzaldehyde; 0.5% of p-hydroxybenzyl methyl ether.

EXAMPLE 39

In a 1 l reactor, an oxygen stream of 5.0 l/h was passed into a mixture of 81 g (0.75 mol) of p-cresol, 250 g of methanol, 60 g (1.5 mol) of sodium hydroxide, 54 g (1.0 mol) of sodium methylate, 0.375 g (0.53 mmol) of iron tetraphenylporphin (in the form of FeTPPCl) and 0.15 g (1.9 mmol) of copper(II) oxide at 60° C. for 8 hours with vigorous stirring. Work-up as in Example 37.

Conversion >99%.

Yield: 85.3% of p-hydroxybenzaldehyde; 2.6% of p-hydroxybenzyl methyl ether.

EXAMPLE 40

Procedure as in Example 39, except that the amount of iron tetraphenylporphin was reduced to 0.075 g (0.11 mmol).

Conversion >99%.

Yield: 86.1% of p-hydroxybenzaldehyde; 1.7% of p-hydroxybenzyl methyl ether.

EXAMPLES 41–47

In a 1 l reactor, an oxygen stream of 4.0 l/h was passed into a mixture of 54.0 g (0.50 mol) of p-cresol, 250 g of methanol, 50 g (1.25 mol) of sodium hydroxide, 54 g (1.0 mol) of sodium methylate, 0.10 g (1.3 mmol) of copper(II) oxide and 0.07 mmol of iron tetraarylporphin (in the form of FeTAPCl = iron tetraarylporphin, charge balanced by Cl$^-$; TAP = tetraarylphorphin), using the tetraarylporphin systems listed in Table 6 at 60° C. for 7 hours with vigorous stirring. The results are summarized in Table 6. The p-cresol conversion was in each case >99%.

TABLE 6

| Example No. | Tetraarylporphin | Yield % p-HBA | p-HBME |
|---|---|---|---|
| 41 | Tetrakis-(4-methoxyphenyl) porphin | 92.9 | 0.7 |
| 42 | Tetrakis-(3,4-methylenedioxy-phenyl) porphin | 88.4 | 1.4 |
| 43 | Tetrakis-(4-methylphenyl) porphin | 87.7 | 1.1 |
| 44 | Tetrakis-(4-chlorophenyl) porphin | 76.2 | 6.8 |
| 45 | Tetrakis-(2-chlorophenyl) porphin | 83.5 | 0.7 |
| 46 | Tetrakis-(4-t-butylphenyl) porphin | 81.3 | 1.9 |
| 47 | Tetrakis-(2,4-dimethoxyphenyl) porphin | 90.6 | 0.6 |

What is claimed is:

1. A process for the preparation of p-hydroxybenzaldehydes of the formula

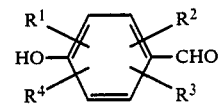

in which

R$^1$ to R$^4$ independently of one another denote hydrogen, halogen, C$_1$–C$_{10}$-alkyl, C$_3$–C$_8$-cycloalkyl, phenyl or C$_1$–C$_{10}$-alkoxy, comprising oxidizing p-cresols of the formula

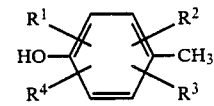

in which

R$^1$ to R$^4$ have the meaning given, with oxygen in the presence of 1–10 equivalents of basic substances per mole of p-cresol in a solvent in the presence of a chelate complex of iron, manganese or iron and manganese wherein the basic substances are metal hydroxides, metal alcoholates or metal amides of alkali metals or alkaline earth metals or alcoholates or amides of aluminum and the reaction is carried out at a temperature of from 0°–200° C.

2. The process of claim 1 wherein the p-cresols oxidized are those of the formula

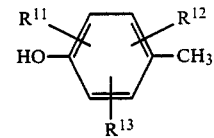

in which

R$^{11}$, R$^{12}$ and R$^{13}$ independently of one another denote hydrogen, fluorine, chlorine, bromine, C$_1$–C$_6$-alkyl, C$_5$–C$_6$-cycloalkyl, phenyl or C$_1$–C$_6$-alkoxy.

3. The process of claim 2 wherein the p-cresols oxidized are those of the formula

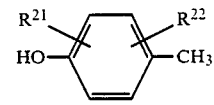

in which

R$^{21}$ stands for hydrogen, fluorine, chlorine, bromine C$_1$–C$_6$-alkyl, cyclohexyl, phenyl or C$_1$–C$_6$-alkoxy, and R$^{22}$ denotes hydrogen, C$_1$–C$_6$-alkyl or C$_1$–C$_6$-alkoxy.

4. The process of claim 1 wherein the chelate forming agent is one of the group of macrocyclic polyethers and polysulfides, porphyrin analogues, macrocycles obtainable by condensation of carbonyl compounds with amines.

5. The process of claim 4 wherein the chelate forming agent is one of the group of porphyrins and related chemically modified systems.

6. The process of claim 5, wherein the chelating agents are porphyrins, azaporphyrins or phthalocyanines.

7. The process of claim 6, wherein the chelates used are iron tetraarylporphins, manganese tetraarylporphins, haemine, iron azaporphyrin, iron phthalocyanine or iron phthalocyanine tetrasulphonate.

8. The process of claim 1 wherein in the chelate complexes free coordination positions are occupied by anions of inorganic and organic acids, by amines or by sulphides.

9. The process of claim 1 wherein the chelate complexes have one or more metal centres and they are monomers, dimers, oligomers or polymers.

10. The process of claim 1, characterized in that 0.000001–0.05 moles of chelate, calculated as metal, are used per mol of p-cresol.

11. The process of claim 10, characterized in that 0.00001–0.005 moles of chelate, calculated as metal, are used per mol of p-cresol.

12. The process of claim 1, characterized in that a co-catalyst is added to the chelate complex in the form of a compound of the metals copper, chromium, manganese, nickel, iron, silver, vanadium, niobium, tantalum, cadmium, cerium or of further lanthanides in an amount of 0.00001–0.1 moles of metal compound per mol of p-cresol.

13. The process of claim 12 wherein the co-catalyst is used in an amount of 0.005–0.01 moles of metal compound.

14. The process of claim 12, characterized in that 0.001–1000 moles of chelate comples are used per mol of co-catalyst.

15. The process of claim 12, characterized in that inorganic salts of copper and/or cerium are used as co-catalyst.

16. The process of claim 1, characterized in that the reaction is carried out in the presence of activated carbon.

17. The process of claim 1 wherein 1.5–6 equivalents of basic substances are used per mole of p-cresol.

18. The process of claim 1, characterized in that the base used is a mixture of an alkali metal hydroxide or alkaline earth metal hydroxide and an alkali metal alcoholate.

19. The process of claim 18, characterized in that the equivalent ratio of alkali metal hydroxide or alkaline earth metal hydroxide to alkali metal alcoholate is 50:1–1:50.

20. The process of claim 1 wherein the solvent is one or more from the group of the alcohols, ethers, halogenated hydrocarbons, amines, amides and sulphoxides.

* * * * *

UNITED STATES PATENT AND TRADEMARK OFFICE
CERTIFICATE OF CORRECTION

PATENT NO. : 4,929,766

DATED : May 29, 1990

INVENTOR(S) : Schnatterer et al.

It is certified that error appears in the above-identified patent and that said Letters Patent is hereby corrected as shown below:

Title Page    [54] Invention: delete " ARE " and substitute -- FOR --

Title Page    FOREIGN PATENT DOCUMENTS: delete " 213544 " and substitute -- 2135443 --

Title Page    FOREIGN PATENT DOCUMENTS: insert -- 0012939, 7/1980, European Pat. Off. -- and -- 1128847, 5/1962, Fed. Rep. of Germany. --

Col. 1, line 1    Delete " ARE " and substitute -- FOR --

Signed and Sealed this

Third Day of March, 1992

*Attest:*

HARRY F. MANBECK, JR.

*Attesting Officer*      *Commissioner of Patents and Trademarks*